US012810647B2

(12) United States Patent
Nakamura et al.

(10) Patent No.: US 12,810,647 B2
(45) **Date of Patent: *Nov. 24, 2026**

(54) BIOINFORMATION ACQUISITION DEVICE

(71) Applicant: PANASONIC INTELLECTUAL PROPERTY MANAGEMENT CO., LTD., Osaka (JP)

(72) Inventors: Hideyuki Nakamura, Fukuoka (JP); Risa Komatsu, Fukuoka (JP); Tadanori Tezuka, Fukuoka (JP); Sugiko Honda, Kanagawa (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 24 days.

This patent is subject to a terminal disclaimer.

(21) Appl. No.: 19/004,685

(22) Filed: Dec. 30, 2024

(65) Prior Publication Data

US 2025/0140015 A1 May 1, 2025

Related U.S. Application Data

(63) Continuation of application No. 18/035,184, filed as application No. PCT/JP2021/040787 on Nov. 5, 2021, now Pat. No. 12,217,532.

(30) Foreign Application Priority Data

Nov. 6, 2020 (JP) ................................ 2020-185816

(51) Int. Cl.
*G06V 40/13* (2022.01)
*A61B 5/1172* (2016.01)
(Continued)

(52) U.S. Cl.
CPC ........ *G06V 40/1318* (2022.01); *A61B 5/1172* (2013.01); *G06V 10/14* (2022.01);
(Continued)

(58) Field of Classification Search
CPC ................................................. G06V 40/1318
See application file for complete search history.

(56) References Cited

U.S. PATENT DOCUMENTS

2003/0016345 A1 1/2003 Nagasaka et al.
2004/0184641 A1 9/2004 Nagasaka et al.
(Continued)

FOREIGN PATENT DOCUMENTS

CN 110807447 2/2020
JP 04-277874 10/1992
(Continued)

OTHER PUBLICATIONS

International Search Report (ISR) from International Searching Authority (Japan Patent Office) in International Pat. Appl. No. PCT/JP2021/040787, dated Jan. 18, 2022, together with an English language translation.

(Continued)

*Primary Examiner* — Y Lee
(74) *Attorney, Agent, or Firm* — Greenblum & Bernstein, P.L.C.

(57) ABSTRACT

A biometric information acquisition device includes a housing. The housing includes a bottom surface side, a top surface side, a front surface side, a back surface side, and an opening in the front surface side between the bottom and top surface sides. The opening defines an imaging space. A camera is disposed in the housing, with the camera being configured to capture an image of a palm of a hand of a user when inserted into the imaging space with the palm facing the top surface side. An illumination is between the top surface side and the opening, with the illumination being configured to illuminate the imaging space from above. A mirror reflects light from the illumination toward the palm,
(Continued)

and a display prompts the user to insert the palm into the imaging space with the palm facing the top surface side.

20 Claims, 11 Drawing Sheets

(51) Int. Cl.
*G06V 10/14* (2022.01)
*G06V 40/60* (2022.01)
*H04N 23/51* (2023.01)

(52) U.S. Cl.
CPC .......... *G06V 40/1312* (2022.01); *G06V 40/67* (2022.01); *H04N 23/51* (2023.01)

(56) References Cited

U.S. PATENT DOCUMENTS

| | | | | |
|---|---|---|---|---|
| 2005/0047632 | A1 | 3/2005 | Miura et al. | |
| 2005/0254690 | A1 | 11/2005 | Nagasaka et al. | |
| 2005/0254695 | A1 | 11/2005 | Nagasaka et al. | |
| 2008/0049981 | A1 | 2/2008 | Nagasaka et al. | |
| 2008/0049982 | A1 | 2/2008 | Nagasaka et al. | |
| 2008/0117409 | A1 | 5/2008 | Nagasaka et al. | |
| 2008/0117410 | A1 | 5/2008 | Nagasaka et al. | |
| 2008/0152195 | A1 | 6/2008 | Nagasaka et al. | |
| 2009/0232362 | A1* | 9/2009 | Otsubo | G06V 10/141 250/208.1 |
| 2009/0252388 | A1 | 10/2009 | Nagasaka et al. | |
| 2010/0085151 | A1 | 4/2010 | Hama et al. | |
| 2011/0176126 | A1 | 7/2011 | Nagasaka et al. | |
| 2012/0050721 | A1 | 3/2012 | Nagasaka et al. | |
| 2013/0216105 | A1 | 8/2013 | Nagasaka et al. | |
| 2014/0126783 | A1 | 5/2014 | Nagasaka et al. | |
| 2014/0198957 | A1* | 7/2014 | Aoki | G06V 10/141 29/428 |
| 2016/0104030 | A1 | 4/2016 | Matsunami | |
| 2016/0256079 | A1 | 9/2016 | Shimano et al. | |
| 2019/0014271 | A1 | 1/2019 | Itoh et al. | |
| 2019/0026453 | A1 | 1/2019 | Choi et al. | |
| 2025/0171057 | A1* | 5/2025 | Nakamura | B61F 5/52 |
| 2025/0338524 | A1* | 10/2025 | Nakamura | H10D 64/111 |
| 2025/0371910 | A1* | 12/2025 | Shen | G06V 40/67 |

FOREIGN PATENT DOCUMENTS

| | | |
|---|---|---|
| JP | 2003-030632 | 1/2003 |
| JP | 2004-049705 | 2/2004 |
| JP | 2004-078791 | 3/2004 |
| JP | 2004-265269 | 9/2004 |
| JP | 2010-092121 | 4/2010 |
| JP | 2016-081116 | 5/2016 |
| JP | 2019-511793 | 4/2019 |
| WO | 2013/005305 | 1/2013 |
| WO | 2017/115512 | 7/2017 |

OTHER PUBLICATIONS

Extended European Search Report (EESR) from European Patent Office (EPO) in European Patent Appl. No. 21889273.5, dated Mar. 18, 2024.

* cited by examiner

BIOINFORMATION ACQUISITION DEVICE

CROSS-REFERENCE TO RELATED APPLICATIONS

This is a continuation of U.S. patent application Ser. No. 18/035,184, filed Jun. 8, 2023, which is a National Phase application of International Patent Application No. PCT/JP2021/040787, filed Nov. 5, 2021, which claims the benefit of priority of Japanese Patent Application No. 2020-185816, filed Nov. 6, 2020. The entire disclosure of each of the above-identified documents, including the specification, drawings, and claims, is incorporated herein by reference in its entirety.

TECHNICAL FIELD

The present disclosure relates to a biometric information acquisition device.

BACKGROUND ART

Patent Literature 1 discloses a multi-faceted stereoscopic imaging device capable of capturing an image of fingerprints and finger veins. The multi-faceted stereoscopic imaging device includes a scan panel upper case that forms a finger-holding portion on upper and lower sides and a scan panel lower case that accommodates an electrical component thereof, and a scan panel that simultaneously captures an image of the fingerprints and the finger veins is installed on an upper portion of the scan panel upper case. In the scan panel, a fingerprint finger contact portion and a finger vein finger non-contact portion form a step in front and back, a groove side wall is formed around the scan panel such that the finger vein finger non-contact portion of the scan panel can be formed by a groove, the finger-holding portion is formed parallel to the fingerprint finger contact portion such that a finger can be placed on an upper end edge around the scan panel, and the image of the fingerprints and the finger veins can be imaged by three CCD cameras. A finger vein camera is built in an object accommodation unit, and captures an image of finger veins of an object at a lower portion and a side surface toward the scan panel, and a fingerprint camera captures an image of fingerprints of the object at the lower portion, thereby simultaneously authenticating the fingerprints and the finger veins.

CITATION LIST

Patent Literature

Patent Literature 1: JP2019-511793T

SUMMARY OF INVENTION

Technical Problem

A biometric authentication device using a finger is mainly a contact-type biometric authentication device that authenticates by fixing a finger such that authentication accuracy does not decrease due to camera shake or the like. However, in the contact-type biometric authentication device, fingerprints of other users may remain on the scan panel, and the authentication accuracy may decrease. In addition, in recent years, there is a growing demand for a biometric authentication device that reduces chances of contact between an unspecified number of people and objects from a sanitary point of view such as virus infection countermeasures. However, in the configuration of Patent Literature 1, since a user brings a tip portion of a finger (for example, vicinity of a first joint to a second joint) into contact with the fingerprint finger contact portion and fixes the finger thereto, there is room for improvement in order to implement acquisition of biometric information in a non-contact manner.

Further, as in the configuration of Patent Literature 1, the biometric authentication device holds a hand so that a palm of the user faces downward (on a side of the biometric authentication device), and captures an image of the fingerprints by illuminating the fingerprints with a light source installed in a direction facing the fingerprints of the held hand. However, when the light source is turned on toward a user side as described above, illumination light of the light source may directly enter eyes of the user and make the user feel dazzled. In addition, when a light amount of the light source is reduced, in the non-contact biometric authentication device, a depth of field of the CCD camera is small, making it difficult to capture an image of the fingerprints, or the imaged fingerprints may not be clear, resulting in a decrease in the authentication accuracy.

The present disclosure has been made in view of the above-described circumstances, and an object of the present disclosure is to provide a biometric information acquisition device that can reduce dazzle due to illumination light at the time of capturing an image of a finger image used for biometric authentication and stably acquire the finger image even in a non-contact manner.

Solution to Problem

The present disclosure provides a biometric information acquisition device including: a camera configured to capture an image of a hand of a user inserted into an imaging space; an illumination configured to illuminate inside of the imaging space from above; a housing configured to accommodate the camera and the illumination; and a first opening formed by cutting out a part of the housing and provided in a substantially rectangular shape in a front view to form the imaging space.

Advantageous Effects of Invention

According to the present disclosure, dazzle due to illumination light at the time of capturing an image of a finger image used for biometric authentication can be reduced, and a finger image can be stably acquired even in a non-contact manner.

DESCRIPTION OF EMBODIMENTS

Hereinafter, embodiments specifically disclosing configurations and operations of a biometric information acquisition device according to the present disclosure will be described in detail with reference to the drawings as appropriate. However, unnecessarily detailed description may be omitted. For example, detailed description of well-known matters and redundant description of substantially the same configuration may be omitted. This is to avoid unnecessary redundancy of the following description and to facilitate understanding of those skilled in the art. The accompanying drawings and the following description are provided for those skilled in the art to fully understand the present disclosure, and are not intended to limit the subject matters described in the claims.

Terms to be used in the following description are merely examples, and are not intended to limit the scope of the present disclosure. For example, the term "biometric information" includes a captured image including a portion of a finger of a user (a finger image) used to extract the biometric information.

In addition, in each drawing in which arrows indicating directions are indicated, an X axis indicates a depth direction. A Y axis indicates a left-right direction. A Z axis indicates an up-down direction (a vertical direction). The X axis and the Y axis are orthogonal to each other and are included in a horizontal plane. The Z axis is included in a vertical plane.

First Embodiment

Figure 1:
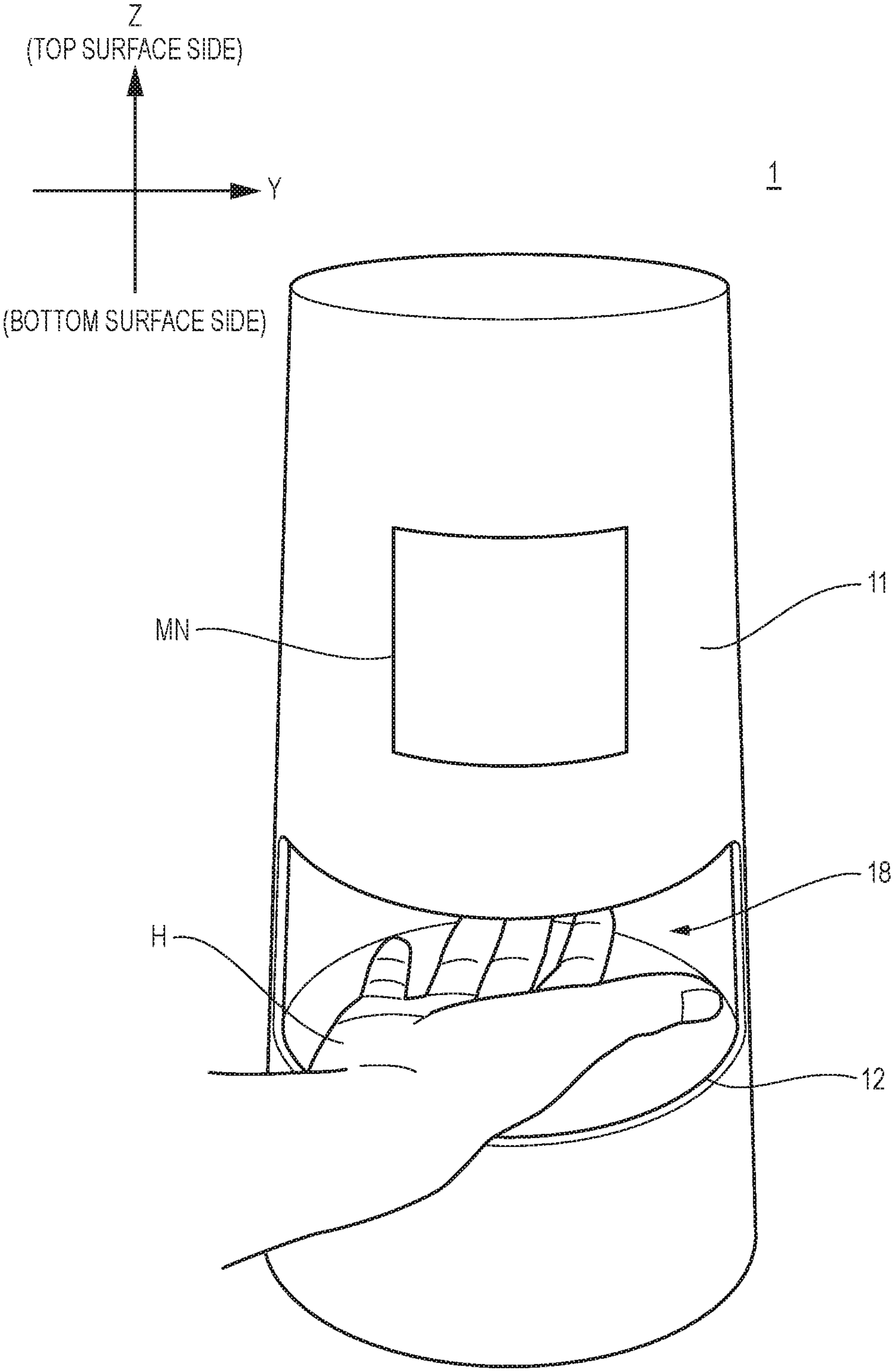
FIG. 1 is a diagram showing a use case of a biometric information acquisition device according to a first embodiment.
Figure 2:
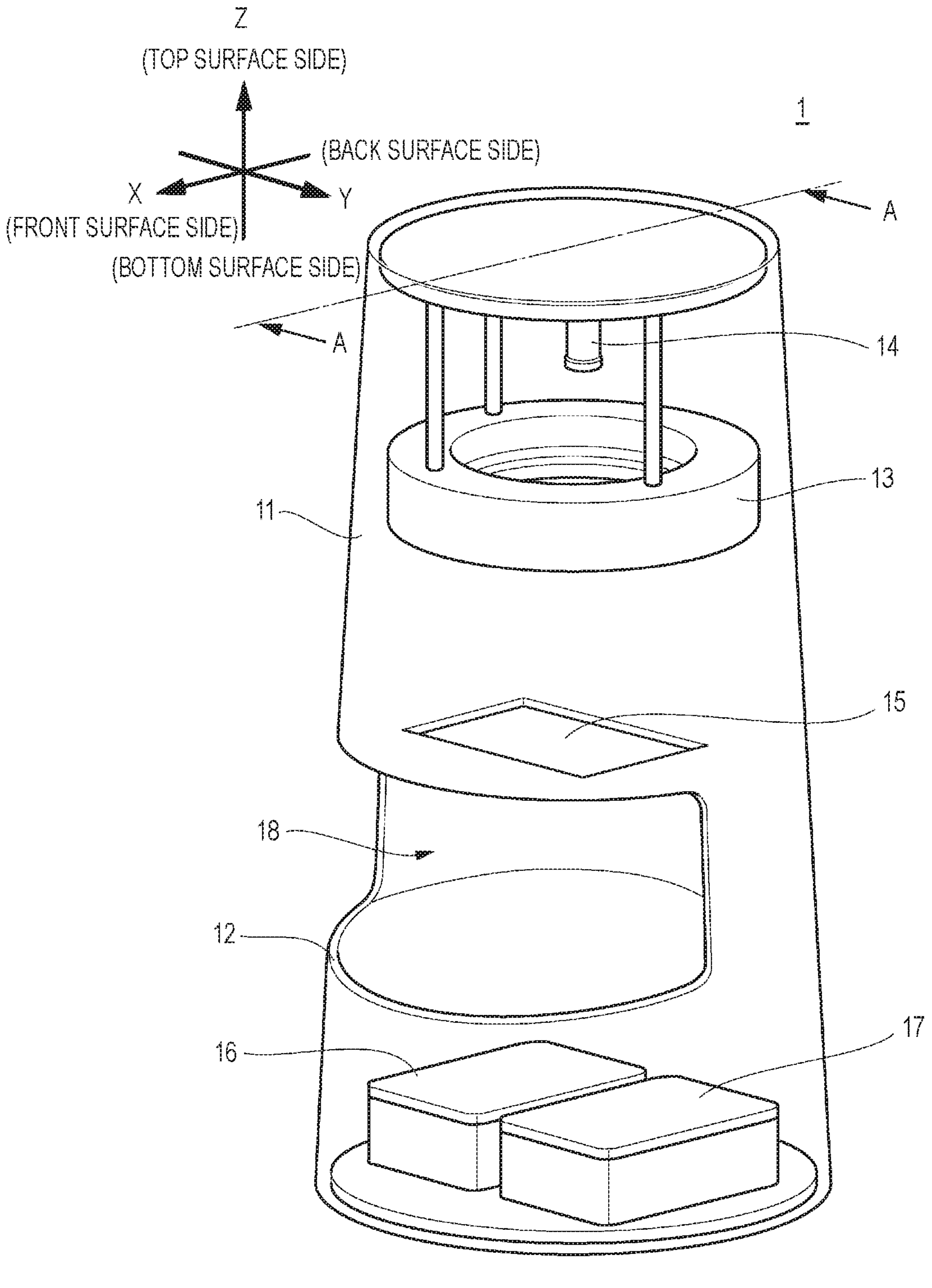
FIG. 2 is a transmission diagram showing a structure of the biometric information acquisition device according to the first embodiment.

A configuration of a biometric information acquisition device 1 according to a first embodiment will be described with reference to FIGS. 1 and 2. FIG. 1 is a diagram showing a use case of the biometric information acquisition device 1 according to the first embodiment. FIG. 2 is a transmission diagram showing a structure of the biometric information acquisition device 1 according to the first embodiment. In the biometric information acquisition device 1 shown in FIG. 2, an illustration of a monitor MN is omitted.

The biometric information acquisition device 1 according to the first embodiment includes a first opening 12 on a front surface side of a housing 11, and illuminates, by an illumination 13 from above, a hand H of a user inserted into an imaging space 18 formed by the first opening 12. The biometric information acquisition device 1 acquires a captured image (hereinafter, referred to as a "finger image") obtained by capturing an image of a part of the hand H or a finger of the user illuminated from above. In addition, the biometric information acquisition device 1 may extract and acquire biometric information on the user by using the captured finger image. The biometric information referred to here may be biometric information based on fingerprints of the user or biometric information based on veins in the finger of the user. The biometric information acquisition device 1 executes user authentication based on the acquired biometric information on the user and outputs an authentication result.

The biometric information acquisition device 1 according to the first embodiment includes the housing 11, the first opening 12, the illumination 13, a camera 14, a second opening 15, a control unit 16, and a power supply unit 17. For example, as shown in FIG. 1, the monitor MN may be provided on a front surface or the like of the housing 11 of the biometric information acquisition device 1, or may be communicably connected as an external connection device of the biometric information acquisition device 1.

The housing 11 is formed of resin or metal in a substantially truncated conical shape. Although the housing 11 of the biometric information acquisition device 1 according to the first embodiment is formed in the truncated conical shape as an example, the present disclosure is not limited thereto, and may be, for example, a cylindrical shape, a cube shape, and a rectangular parallelepiped shape. The housing 11 has the first opening 12 for the user to insert the hand H in the front surface side (in an X direction) of side surfaces of the housing 11. The housing 11 has the second opening 15 above the imaging space 18. The housing 11 may include the monitor MN on the front surface thereof. The housing 11 accommodates the illumination 13, the camera 14, the control unit 16, and the power supply unit 17.

The first opening 12 is formed in a substantially rectangular shape in a front view of the biometric information acquisition device 1 by cutting out a part of the housing 11, and is formed in a shape of, for example, a substantially rectangular shape or a substantially elliptical shape such that the hand H of the user can be inserted from the front surface toward a back surface side. An opening peripheral edge portion of the first opening 12 is subjected to an R-chamfering process. Opening examples of the first opening 12 will be described with reference to FIG. 5 to be described later.

The illumination 13 includes, for example, one or more illuminations such as a light emitting diode (LED), a fluorescent lamp, an incandescent lamp, and an infrared (IR) illumination. The illumination 13 turns on or off the illumination based on a control command (a control signal) output from the control unit 16. Although the illumination 13 according to the first embodiment is formed in a substantially annular shape as an example in FIG. 2, the present disclosure is not limited thereto. For example, the illumination 13 may be a point light source, or may have a configuration in which a plurality of illuminations are disposed in a substantially polygonal shape or a substantially annular shape. The illumination 13 is accommodated in the housing 11 of the biometric information acquisition device 1, and illuminates, from above, the hand H of the user inserted into the imaging space 18. Accordingly, since the illumination light of the illumination 13 does not directly enter eyes of the user, the user can use the biometric information acquisition device 1 without feeling dazzled.

The illumination 13 shown in FIG. 2 is installed between the camera 14 and the second opening 15 as an example, and is not limited thereto. For example, when the second opening 15 is not formed in the housing 11, the illumination 13 may be installed on an upper side (in a Z direction) in the imaging space 18 formed by the first opening 12.

The camera 14 includes at least an image sensor (not shown) and a lens (not shown). The image sensor is, for example, a solid-state imaging element such as a charged-coupled device (CCD) or a complementary metal oxide semi-conductor (CMOS), and converts an optical image formed on an imaging surface into an electric signal. The camera 14 is accommodated in the housing 11 of the biometric information acquisition device 1, and captures an image of a part of the hand H or the finger of the user inserted into the imaging space 18 from above.

The camera 14 shown in FIG. 2 is installed on a back surface of a surface of the housing 11 on a top side as an example, and is not limited thereto. For example, the camera 14 may be disposed closer to a bottom surface side than the illumination 13 (that is, between the illumination 13 and the second opening 15), or may be disposed above the imaging space 18 formed by the first opening 12 when the second opening 15 is not formed.

Installation positions of the illumination 13 and the camera 14 shown in FIG. 2 and an arrangement relationship therebetween are merely examples, and the present disclosure is not limited thereto. For example, the camera 14 may be installed at a position lower than the illumination 13 in the Z direction. In addition, an example in which the illumination 13 shown in FIG. 2 is suspended from a surface on a −Z direction side of a top surface of the housing 11 is shown, and the illumination 13 may be fixed and installed on an inner side of the side surface of the housing 11 to illuminate a part of the hand H or the finger of the user inserted into the imaging space 18 from obliquely above. Similarly, an example in which the camera 14 shown in FIG. 2 is fixed and installed on the surface on the −Z direction side of the top surface of the housing 11 is shown, and the camera 14 may be fixed and installed on an inner side of the side surface of the housing 11 to capture an image of a part of the hand H or the finger of the user inserted into the imaging space 18 from obliquely above.

The second opening 15 is formed above the imaging space 18 (for example, between the illumination 13 or the camera 14 and the imaging space 18) by cutting out a part of the housing 11. The second opening 15 allows the illumination light from the illumination 13 to illuminate the hand H of the user inserted into the imaging space 18 from above. In addition, the second opening 15 allows the camera 14 to capture an image of the hand H of the user inserted into the imaging space 18 from above.

The control unit 16, which is an example of a gravity center portion, is accommodated below the imaging space 18, that is, on the bottom surface side of the housing 11, executes control of the illumination 13 and the camera 14, and executes imaging of a finger image of the user for biometric authentication (that is, acquisition of the biometric information) or extraction of the biometric information on the user using the captured finger image. The control unit 16 extracts the biometric information on the user by using the captured finger image, and executes collation between the extracted biometric information on the user with biometric information on each of a plurality of users registered in advance (user authentication). In addition, since the control unit 16 is accommodated in the imaging space 18 (that is, on the bottom surface side of the housing 11), a height of a center of gravity of the biometric information acquisition device 1 can be adjusted to a lower position (that is, the bottom surface side of the housing 11). Accordingly, even when an external force is applied to the side surface of the housing 11 (for example, when the hand H of the user comes into contact with or collides with the side surface of the housing 11), the biometric information acquisition device 1 is less likely to fall down.

The power supply unit 17 as an example of the gravity center portion is accommodated below the imaging space 18, that is, on the bottom surface side of the housing 11, and supplies electric charges supplied from an external commercial power source to the illumination 13, the camera 14, and the control unit 16. In addition, the power supply unit 17 may include a battery (for example, a cell) capable of accumulating the electric charges supplied from the external commercial power source, and may be implemented to be detachable from the battery. In addition, since the power supply unit 17 is accommodated in the imaging space 18 (that is, on the bottom surface side of the housing 11), a height of the center of gravity of the biometric information acquisition device 1 can be adjusted to a lower position (that is, the bottom surface side of the housing 11). Accordingly, even when an external force is applied to the side surface of the housing 11 (for example, when the hand H of the user comes into contact with or collides with the side surface of the housing 11), the biometric information acquisition device 1 is less likely to fall down.

The biometric information acquisition device 1 may further include a weight (not shown) as an example of the gravity center portion for adjusting the height of the center of gravity of the biometric information acquisition device 1, which is accommodated in the housing 11 and located closer to the bottom surface side than the imaging space 18.

The monitor MN as an example of a display unit is implemented using, for example, a liquid crystal display (LED) or an organic electroluminescence (EL). The monitor MN displays a collation result output from a processor 21, or outputs sound by a speaker (not shown). The monitor MN may be implemented integrally with the biometric information acquisition device 1 or may be implemented as a separate body.

The biometric information acquisition device 1 may include a sensor (not shown) that detects insertion of the hand H of the user into the imaging space 18. In such a case, the sensor is disposed in the front surface of the housing 11 (for example, above the first opening 12). Specifically, the sensor is a reflection-type time of flight (TOF) sensor, an infrared sensor, a transmission-type laser sensor, a light receiving sensor, or the like, and when the hand H of the user inserted into the imaging space 18 is detected, the sensor generates a detection signal and outputs the detection signal to the processor 21.

Figure 3:
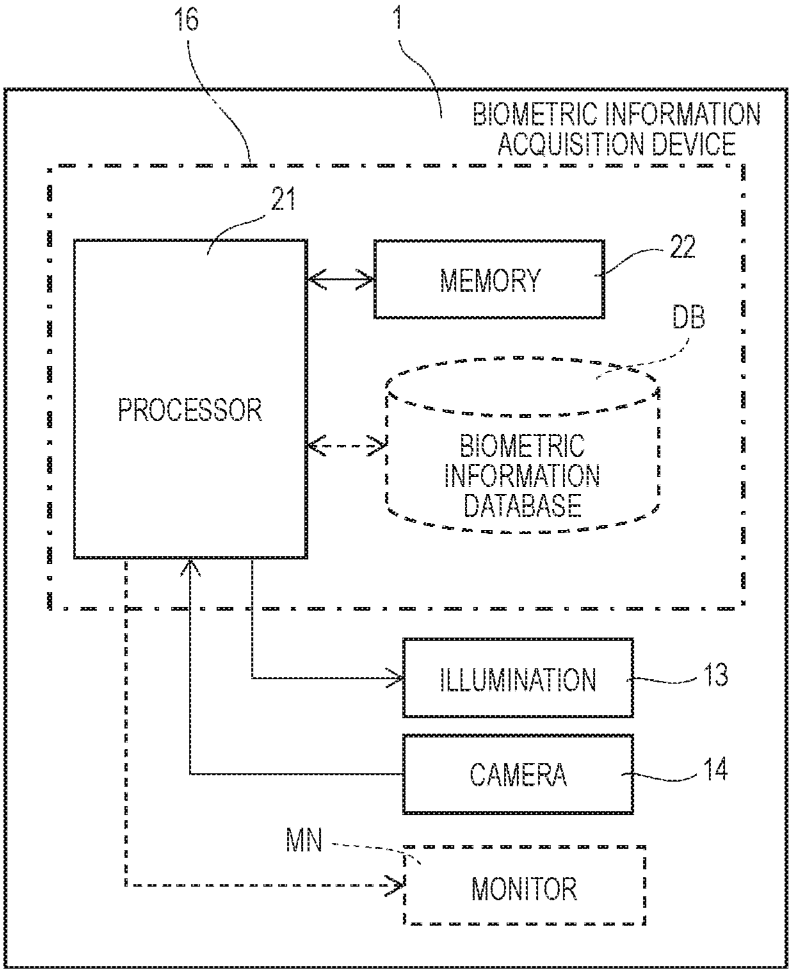
FIG. 3 is a diagram showing a functional configuration example of the biometric information acquisition device according to the first embodiment.

Next, a functional configuration of the biometric information acquisition device 1 according to the first embodiment will be described with reference to FIG. 3. FIG. 3 is a diagram showing the functional configuration example of the biometric information acquisition device 1 according to the first embodiment. In the functional configuration of the biometric information acquisition device 1 shown in FIG. 3, a biometric information database DB need not be an essential configuration and may be omitted.

The processor 21 is implemented by using, for example, a central processing unit (CPU) or a field programmable gate array (FPGA), and executes various kinds of processing and controls in cooperation with a memory 22. Specifically, the processor 21 executes a program by referring to a program and data held in the memory 22, thereby implementing a function of each unit for acquiring the finger image of the user or the biometric information on the user. Specifically, the processor 21 executes control of turning-on and turningoff of the illumination 13, control related to imaging of the camera 14, and the like. When the biometric information acquisition device 1 executes user authentication processing based on the biometric information on the user, the processor 21 may implement the function of each unit necessary for executing the user authentication processing.

The memory 22 includes, for example, a random access memory (RAM) as a work memory used when each processing of the processor 21 is executed, and a read only memory (ROM) storing a program and data defining an operation of the processor 21. The RAM temporarily stores data or information generated or acquired by the processor 21. The program that defines the operation of the processor 21 is written into the ROM.

The biometric information database DB is a storage medium device such as a hard disk drive (HDD) or a solid state drive (SSD), and stores biometric information on a plurality of users registered by an administrator in advance (for example, a specific person such as a security guard or an administrator of a facility or a building where the biometric information acquisition device 1 is installed, or an employee of a store where the biometric information acquisition device 1 is installed). The biometric information stored in the biometric information database DB is biometric information that can be biometrically authenticated based on fingerprints or veins of each of a plurality of fingers of the user, and is stored in association with information on the user. Although an example in which the biometric information database DB shown in FIG. 2 is integrally formed with the biometric information acquisition device 1 is illustrated, the biometric information database DB is configured as an external storage device that is implemented separately from the biometric information acquisition device 1 and is externally connected to be capable of data communication.

Figure 4:
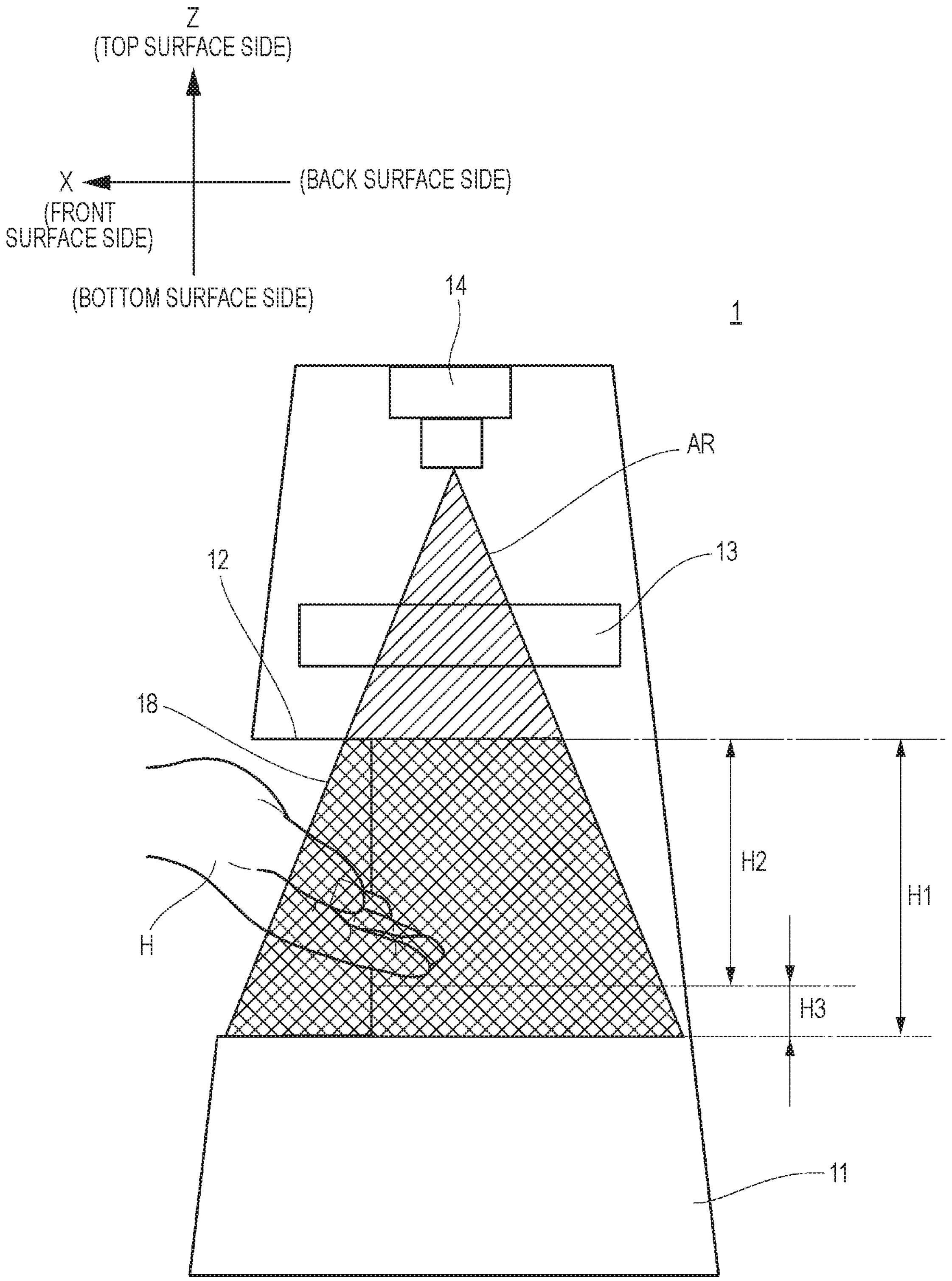
FIG. 4 is a cross-sectional view taken along a line A-A of the biometric information acquisition device shown in FIG. 2.

Here, the imaging space 18 will be described with reference to FIG. 4. FIG. 4 is a cross-sectional view taken along a line A-A of the biometric information acquisition device 1 shown in FIG. 2. In addition, the biometric information acquisition device 1 shown in FIG. 4 is a cross-sectional view viewed from a Y direction. In the biometric information acquisition device 1 shown in FIG. 4, an illustration of the control unit 16 and the power supply unit 17 is omitted. In the example shown in FIG. 4, the illumination 13 and the camera 14 are disposed above the imaging space 18 (in the Z direction), and may be disposed on an upper side in the imaging space 18.

The camera 14 is capable of capturing an image of an imaging region AR, and has a depth of field H2 as a region in the Z direction capable of extracting biometric information such as fingerprints and veins in the imaging region AR and capable of capturing an image of a finger image that can be used for biometric authentication. The camera 14 captures an image of the hand H (fingers) of the user (more specifically, a part of the hand H or the fingers of the user positioned at a height of the depth of field H2 in the imaging space 18) inserted into the imaging space 18 which is a region based on the depth of field H2 and an angle of view.

The imaging space 18 is formed such that the hand H of the user can be inserted through the first opening 12. A height H1 of the imaging space 18 in the Z direction is a height equal to or greater than a thickness H3 of a general human finger or a height equal to or smaller than the depth of field H2 of the camera 14. A maximum value of the height H1 of the imaging space 18 in the Z direction is equal to a total height of the depth of field H2 of the camera 14 and the thickness H3 of a general human finger. The height H1 of the imaging space 18 shown in FIG. 4 is, for example, equal to an opening height of the first opening 12 in the Z direction, and the height H1 is not limited thereto. The height H1 of the imaging space 18 may be formed to be higher than the height of the first opening 12 in the Z direction, and the illumination 13, the camera 14, or both the illumination 13 and the camera 14 may be installed inside the imaging space 18.

Here, the depth of field H2 of the camera 14 will be described. The depth of field H2 indicates a distance (that is, a range) in which the captured finger image is focused in an imaging direction of the camera 14 (in a −Z direction in the example shown in FIG. 4). That is, when the hand (the fingers) of the user is inserted into the imaging space 18, the camera 14 can capture a finger image that can be used for the biometric authentication by focusing on the fingers of the hand H of the user. The depth of field H2 increases as a focal length of a lens (not shown) of the camera 14 decreases, and increases as an aperture value (an F value) of the lens increases.

Figure 5:
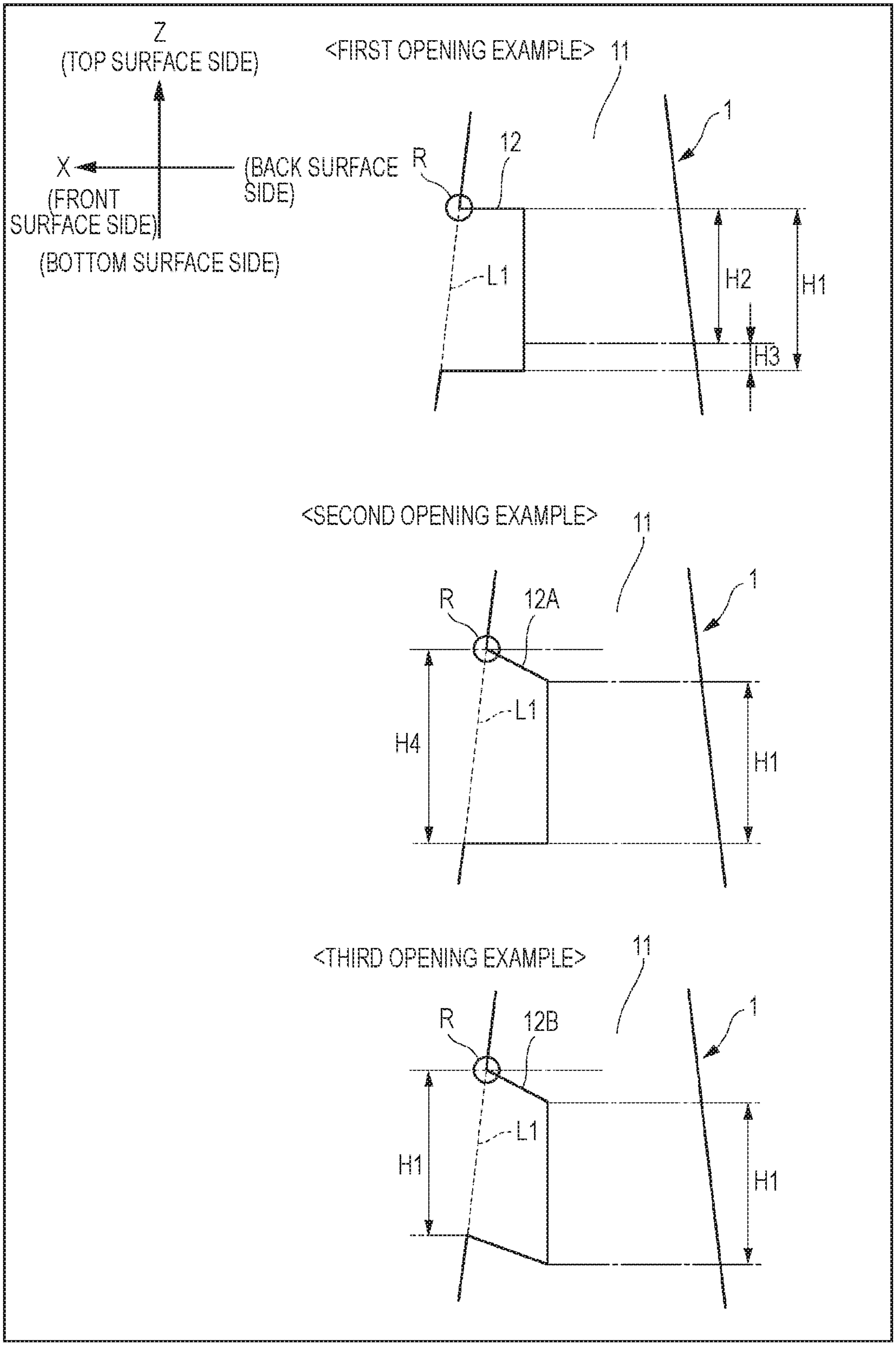
FIG. 5 is a diagram showing opening examples of a first opening.

Next, opening examples of the first opening 12 will be described with reference to FIG. 5. FIG. 5 is a diagram showing the opening examples of the first opening 12. The biometric information acquisition device 1 shown in FIG. 5 is a side view of the biometric information acquisition device 1 as viewed from the Y direction. In addition, in order to make the description easy to understand, the biometric information acquisition device 1 shown in FIG. 5 omits the illustration of the entire biometric information acquisition device 1, and illustrates only relevant parts including the first opening 12. Further, a peripheral edge portion R shown in each of the first openings 12, 12A, and 12B indicates at least a peripheral edge portion of an opening upper end in a side view. The peripheral edge portion R is subjected to the R-chamfering process.

Auxiliary lines L1 shown in FIG. 5 are lines indicating an outer shape (a surface) of the housing 11 when the first opening 12 is not formed.

The first opening 12 shown in a first opening example is formed such that peripheral edges of the first opening 12 form a U-shape in the side view (that is, as viewed from the Y direction) (in other words, the auxiliary line L1 and the peripheral edges of the first opening 12 form a substantially rectangular shape when viewed from the Y direction).

The first opening 12A shown in a second opening example is formed such that the auxiliary line L1 and the peripheral edges of the first opening 12 form a substantially trapezoidal shape in the side view (that is, as viewed from the Y direction). The first opening 12A is formed such that an opening height H4 in the Z direction on the front surface of the housing 11 is the highest, and an opening height in the Z direction is lower toward the back surface side. That is, as shown in FIG. 5, the opening height H4 of the first opening 12A in the front surface of the housing 11 is formed to be higher than the opening height on the back surface side of the first opening 12A (the height H1 of the imaging space 18). In addition, since the first opening 12A is formed at a position closer to a top surface side of the housing 11 as the first opening 12A is on the front surface side of the housing 11, the user can easily insert the hand H into the imaging space 18 without hitting the housing 11 with the hand H. Accordingly, the biometric information acquisition device 1 can further prevent the falling down caused by the hand of the user hitting the housing 11.

The first opening 12B shown in a third opening example is formed such that the auxiliary line L1 and the peripheral edges of the first opening 12B form a substantially parallelogram shape in the side view (that is, as viewed from the Y direction). The first opening 12B is formed such that an opening position in the Z direction on the front surface of the housing 11 is the highest, and the opening position is lower toward the back surface side. Since the first opening 12B is formed at a position closer to a top surface side of the housing 11 as the first opening 12B is on the front surface side of the housing 11, the user can easily insert the hand H into the imaging space 18 without hitting the housing 11 with the hand H. Accordingly, the biometric information acquisition device 1 can further prevent the falling down caused by the hand of the user hitting the housing 11.

Figure 6:
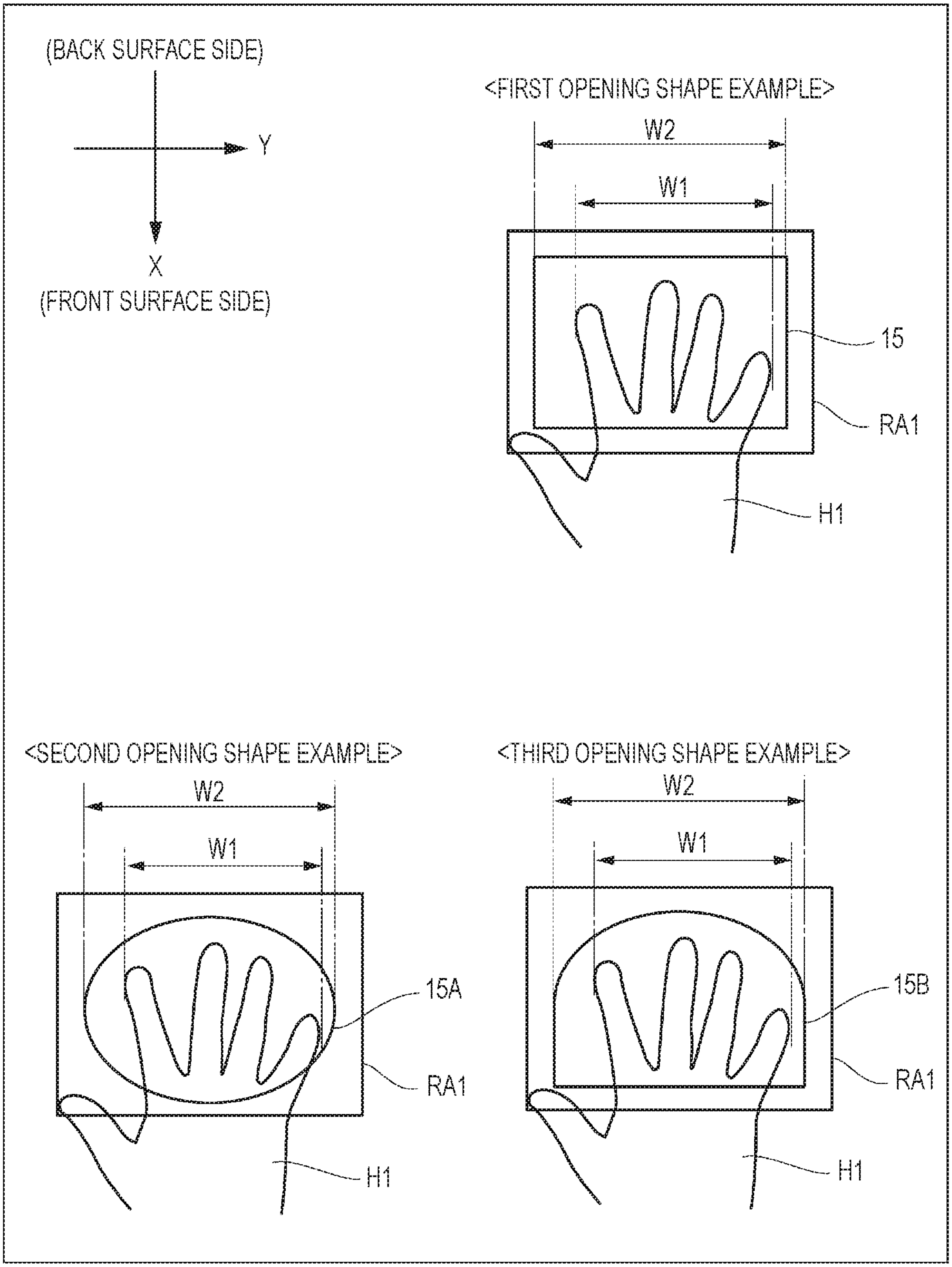
FIG. 6 is a diagram showing opening shape examples of a second opening.

Next, opening shape examples of the second opening 15 will be described with reference to FIG. 6. FIG. 6 is a diagram showing the opening shape examples of the second opening 15. FIG. 6 is a diagram of the second opening 15 viewed from the Z direction.

A width W1 shown in FIG. 6 is a width from an index finger to a little finger of a general human hand H. An opening width W2 indicates an opening length of the second opening 15 in the Y direction. A region RA1 indicates an illumination irradiation range of the illumination 13 or an angle of view of the camera 14. An opening area of the second opening 15 is formed within the region RA1 and is smaller than the region RA1.

The second opening 15 shown in a first opening shape example is formed in a substantially rectangular shape. A second opening 15A shown in a second opening shape example is formed in a substantially elliptical shape. A second opening 15A shown in a third opening shape example is formed in a substantially semicircular shape, a shape obtained by cutting an ellipse in half in a longitudinal direction, or the like. Opening shapes of the second opening shown in FIG. 6 are not limited thereto. For example, the second opening may have a substantially perfect circular shape or a substantially square shape.

Figure 7:
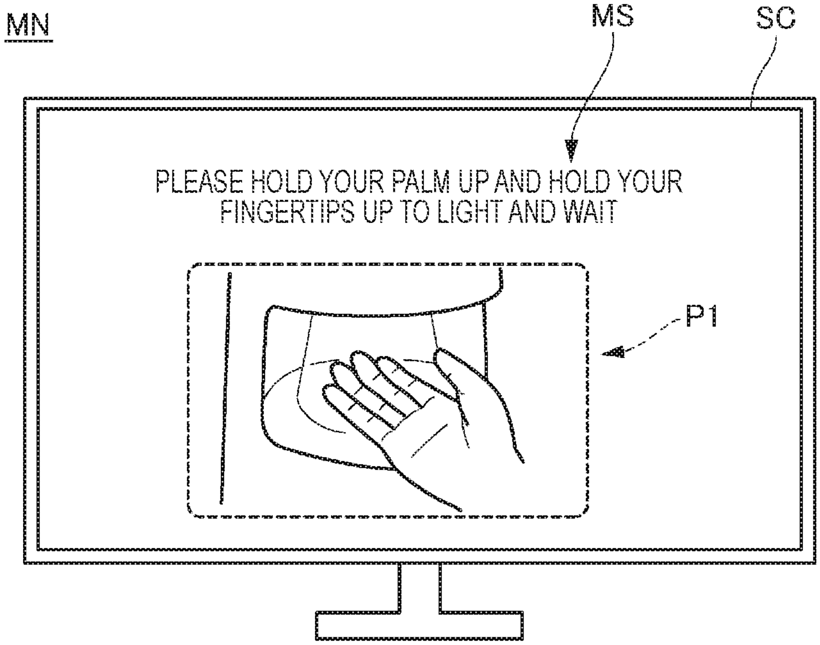
FIG. 7 is a diagram showing an example of a guidance screen.

Next, a guidance screen SC displayed on the monitor MN for the user to insert the hand H into the imaging space 18 will be described with reference to FIG. 7. FIG. 7 is a diagram showing an example of the guidance screen SC. The monitor MN shown in FIG. 7 is an example that is separately implemented as an external connection device of the biometric information acquisition device 1.

The monitor MN displays the guidance screen SC for prompting the user to insert the hand H in order to capture an image of (acquire) the finger image of the user as the biometric information. The guidance screen SC is generated by the processor 21, and is output from a communication unit (not shown) of the biometric information acquisition device 1 to the monitor MN and displayed.

The guidance screen SC is generated including a message MS "Please hold your palm up and hold your fingertips up to light and wait" that prompts the user to insert the hand H and an illustration PI showing the user an image of inserting the hand H into the imaging space 18. The guidance screen SC shown in FIG. 7 is an example, and the present disclosure is not limited thereto. The guidance screen SC may include only one of the message MS and the illustration PI. Further, the message MS may be output by sound by a speaker (not shown) of the monitor MN.

Figure 8:
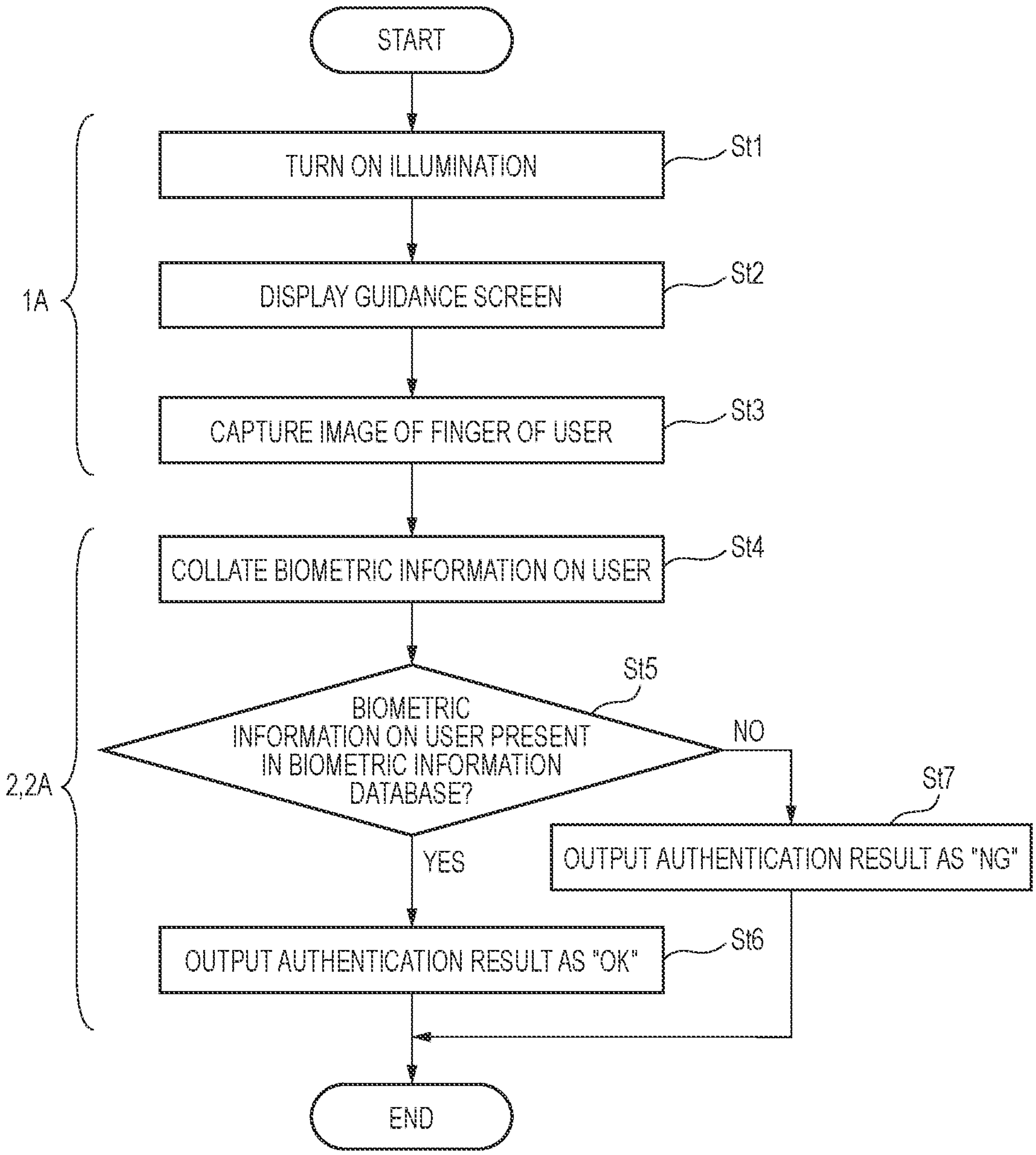
FIG. 8 is a flowchart showing an example of an operation procedure of the biometric information acquisition device according to the first embodiment.

A processing procedure of the biometric information acquisition device 1 according to the first embodiment will be described with reference to FIG. 8. FIG. 8 is a flowchart showing an example of an operation procedure of the biometric information acquisition device 1 according to the first embodiment. In the flowchart shown in FIG. 8, an example is shown in which the biometric information acquisition device 1 extracts the biometric information using the finger image as the biometric information acquired as an example, and executes the user authentication based on the extracted biometric information, and biometric information extraction processing and user authentication processing may be omitted, and processing up to acquisition of the finger image may be executed.

When the user authentication is started, the biometric information acquisition device 1 turns on the illumination 13 (St1). The biometric information acquisition device 1 generates the guidance screen SC and displays the guidance screen SC on the monitor MN (St2).

The biometric information acquisition device 1 captures, by the camera 14, an image of the hand (a part of the finger) of the user inserted into the imaging space 18 (St3), and extracts the biometric information on the user based on the captured finger image of the user. The biometric information acquisition device 1 collates the extracted biometric information on the user with biometric information on each of a plurality of users stored (registered) in the biometric information database DB (St4). The biometric information on the user using the finger image of the user may be extracted and collated by a known technique (for example, a technique disclosed in JP2018-124999A).

In the processing of step St4, the biometric information acquisition device 1 determines whether the extracted biometric information on the user is present in the biometric information on the plurality of users stored (registered) in the biometric information database DB (St5).

When it is determined in the processing of step St5 that the extracted biometric information on the user is present in the biometric information on the plurality of users stored (registered) in the biometric information database DB (St5, YES), the biometric information acquisition device 1 outputs an authentication result of the user authentication as "OK" (St6). On the other hand, when it is determined in the processing of step St5 that the extracted biometric information on the user is not present in any of the biometric information on the plurality of users stored (registered) in the biometric information database DB (St5, NO), the biometric information acquisition device 1 outputs the authentication result of the user authentication as "NG" (St7). The biometric information acquisition device 1 may generate a screen indicating that the authentication result of the user authentication is "OK" or the authentication result is "NG", output and display the screen on the monitor MN, or may output sound by a speaker (not shown) of the monitor MN.

As described above, the biometric information acquisition device 1 according to the first embodiment can prevent the illumination light of the illumination 13 from directly entering the eyes of the user by illuminating, by the illumination 13 from above, a part of the hand H or the finger of the user accommodated in the housing 11. In addition, since the illumination light of the illumination 13 does not directly enter the eyes of the user, the biometric information acquisition device 1 can increase the light amount of the illumination 13. Accordingly, the biometric information acquisition device 1 can increase the height H1 of the imaging space 18 in the Z direction by setting the F value of the lens of the camera 14 to be large and increasing the depth of field H2, and the user can easily insert or hold the hand in the imaging space 18. In addition, since an exposure time of the camera 14 can be set shorter by increasing the light amount of the illumination 13, the biometric information acquisition device 1 can capture an image of the finger image with reduced camera shake even in a state in which the hand of the user is not completely stationary. Therefore, since the biometric information acquisition device 1 can capture an image of the finger image for the biometric authentication even when the hand H or a part of the finger of the user is imaged in a non-contact state, it is possible to improve authentication accuracy of the biometric authentication using the biometric information. Further, the biometric information acquisition device 1 can capture an image of the finger image in which the camera shake is reduced, thereby preventing occurrence of re-imaging and shortening a time for the user to hold the hand H, thereby further improving usability.

In addition, since the biometric information acquisition device 1 according to the first embodiment is installed such that the camera 14 is directed downward (in the −Z direction), dirt such as dust is less likely to adhere to the lens of the camera 14, and it is possible to prevent a decrease in the authentication accuracy of biometric authentication using the biometric information.

Second Embodiment

The biometric information acquisition device 1 according to the first embodiment described above is an example in which the illumination 13 and the camera 14 are disposed above the imaging space 18, and a finger image of the hand H of the user inserted into the imaging space 18 is imaged. An example will be described in which the biometric information acquisition device 1 according to a second embodiment captures an image of a finger image of the hand H of the user inserted into the imaging space 18 using a mirror 19.

The biometric information acquisition device 1 according to the second embodiment further accommodates the mirror 19 in the housing 11, and a part of a finger UH of the user reflected on the mirror 19 is imaged by the camera 14. The biometric information acquisition device 1 according to the second embodiment reflects illumination light of the illumination 13 by the mirror 19, and illuminates the hand H of the user from above the imaging space 18. The biometric information acquisition device 1 according to the second embodiment illuminates the hand H of the user from above the imaging space 18 by the mirror 19 reflecting the illumination light of the illumination 13, and captures an image of the hand H of the user illuminated and reflected on the mirror 19 by the camera 14.

The mirror 19 is installed above the imaging space 18 or above the second opening 15. The mirror 19 is installed such that an imaging distance between an image sensor (not shown) included in the camera 14 and a surface of the finger UH of the user is a predetermined distance L. Here, the predetermined distance L is a distance at which the finger image of the user inserted into the imaging space 18 can be imaged, and is a distance at which the height H1 of the imaging space 18 is substantially the depth of field H2 of the camera 14 or a distance at which the height H1 of the imaging space 18 is a substantially total value of the depth of field H2 of the camera 14 and the thickness H3 of the finger.

Figure 9:
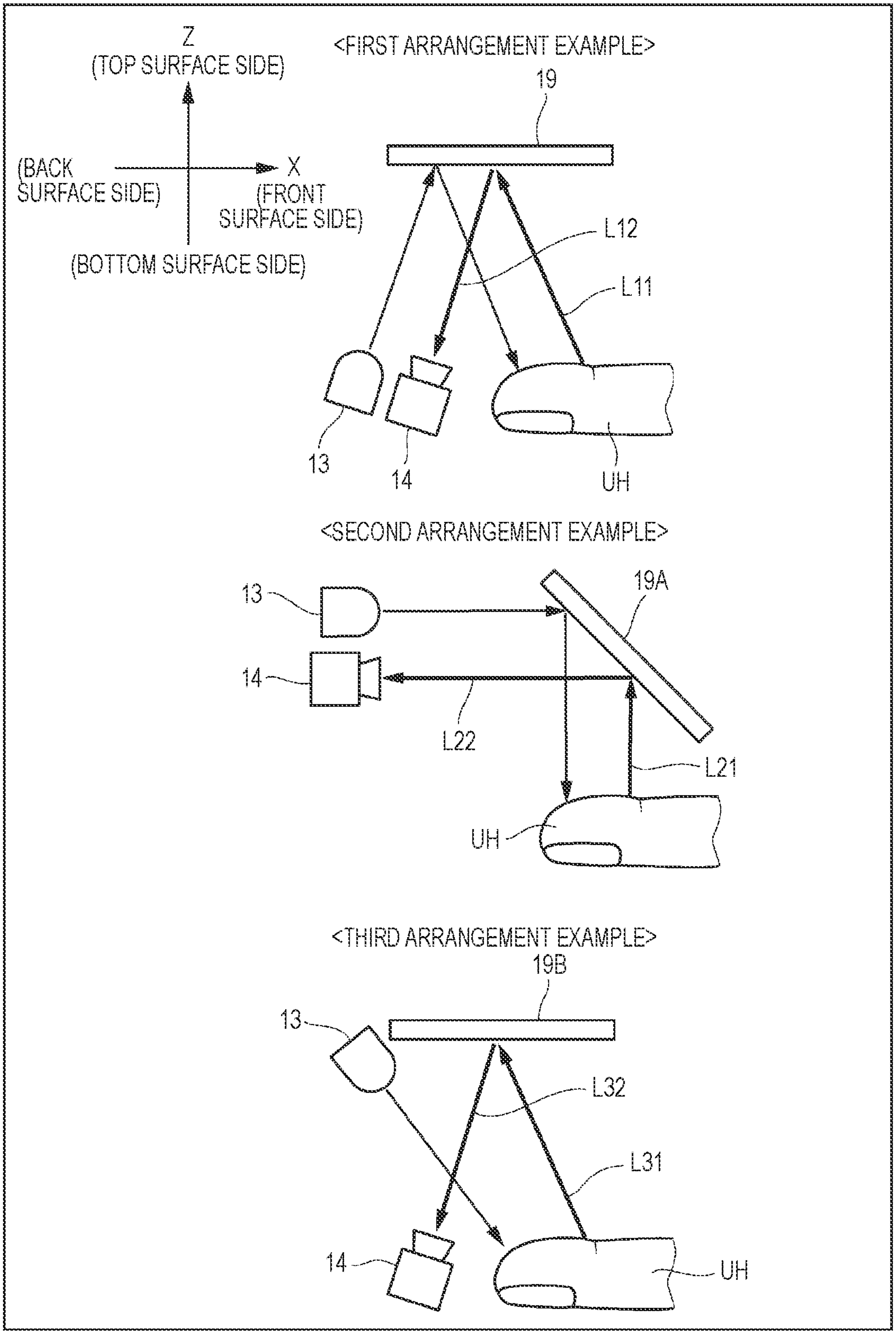
FIG. 9 is a diagram showing arrangement examples of an illumination, a camera, and a mirror in the biometric information acquisition device according to a second embodiment.

Here, arrangement examples of the mirror 19 will be described with reference to FIG. 9. FIG. 9 is a diagram showing the arrangement examples of the illumination 13, the camera 14, and the mirror 19 in the biometric information acquisition device 1 according to the second embodiment. It is needless to say that the illumination 13 shown in FIG. 9 is, for example, a point light source, and the present disclosure is not limited thereto.

The mirror 19 shown in a first arrangement example is installed such that a total of a distance L11 between the finger UH of the user and a surface of the mirror 19 (a surface facing the finger UH of the user) and a distance L12 between an image sensor (not shown) of the camera 14 and the surface of the mirror 19 is the predetermined distance L. The mirror 19 reflects the illumination light of the illumination 13 to illuminate the finger UH of the user. The camera 14 captures an image of the finger UH of the user illuminated by the illumination 13 reflected on the mirror 19.

Although the mirror 19 shown in the first arrangement example is installed to be substantially horizontal to an installation surface of the housing 11, the present disclosure is not limited thereto. The mirror 19 may be installed at an angle at which the surface of the finger UH of the user inserted into the imaging space 18 can be more appropriately imaged depending on the shape of the first opening 12 or the imaging space 18. Accordingly, the biometric information acquisition device 1 can more appropriately capture an image of the surface of the finger UH reflected in the finger image imaged by the camera 14, and thus it is possible to acquire more accurate biometric information on the user (the finger image or the biometric information) for biometric authentication. Therefore, the biometric information acquisition device 1 can further improve the authentication accuracy of the user authentication using the biometric information.

A mirror 19A shown in a second arrangement example is installed such that a total of a distance L21 between the finger UH of the user and a surface of the mirror 19A (a surface facing the finger UH of the user) and a distance L22 between an image sensor (not shown) of the camera 14 and the surface of the mirror 19A is the predetermined distance L. The mirror 19A reflects the illumination light of the illumination 13 to illuminate the finger UH of the user. The camera 14 captures an image of the finger UH of the user illuminated by the illumination 13 reflected on the mirror 19A.

A mirror 19B shown in a third arrangement example is installed such that a total of a distance L31 between the finger UH of the user and a surface of the mirror 19B (a surface facing the finger UH of the user) and a distance L32 between an image sensor (not shown) of the camera 14 and the surface of the mirror 19B is the predetermined distance L. The mirror 19B reflects the finger UH of the user illuminated from above by the illumination 13. The camera 14 captures an image of the finger UH of the user illuminated by the illumination 13 reflected on the mirror 19B.

Although the mirror 19 shown in the first arrangement example and the mirror 19B shown in the third arrangement example are installed to be substantially horizontal to the installation surface of the housing 11, the present disclosure is not limited thereto. The mirror 19B may be installed at an angle at which the surface of the finger UH of the user inserted into the imaging space 18 can be more appropriately imaged depending on the shape of the first opening 12 or the imaging space 18. Accordingly, the biometric information acquisition device 1 can more appropriately capture an image of the surface of the finger UH reflected in the finger image imaged by the camera 14, and thus it is possible to acquire more accurate biometric information on the user (the finger image or the biometric information) for biometric authentication. Therefore, the biometric information acquisition device 1 can further improve the authentication accuracy of the user authentication using the biometric information.

Although the mirror 19A shown in the second arrangement example is installed at approximately 45 degrees with respect to the installation surface of the housing 11, the present disclosure is not limited thereto. The mirror 19A may be installed at an angle at which the surface of the finger UH of the user inserted into the imaging space 18 can be more appropriately imaged depending on the shape of the first opening 12 or the imaging space 18. Accordingly, the biometric information acquisition device 1 can more appropriately capture an image of the surface of the finger UH reflected in the finger image imaged by the camera 14, and thus it is possible to acquire more accurate biometric information on the user (the finger image or the biometric information) for biometric authentication. Therefore, the biometric information acquisition device 1 can further improve the authentication accuracy of the user authentication using the biometric information.

Further, the illumination 13 and the camera 14 shown in the first arrangement example and the second arrangement example are installed (disposed) adjacent to each other, and the arrangement is not limited thereto. The illumination 13 according to the second embodiment may be installed at a position where the illumination 13 can illuminate the finger UH of the user from above, and for example, the illumination 13 may be installed at a position higher than the mirror 19 in the Z direction.

As described above, since the camera 14 according to the second embodiment can secure a sufficient imaging distance (that is, the predetermined distance L) by capturing an image of the hand H or the finger UH of the user reflected on the mirror 19, it is possible to reduce a size of the biometric information acquisition device 1 while maintaining the height of the depth of field H2.

In addition, as compared with the biometric information acquisition device 1 according to the first embodiment shown in FIG. 2, the biometric information acquisition device 1 according to the second embodiment can dispose the illumination 13 and the camera 14 on the bottom surface side of the housing 11, such that a height dimension of the housing 11 in the Z direction can be further reduced, and a height of the center of gravity of the housing 11 can be lowered toward the bottom surface side (the −Z direction). Accordingly, even when an external force is applied to the side surface of the housing 11 (for example, when the hand H of the user comes into contact with or collides with the side surface of the housing 11), the biometric information acquisition device 1 according to the second embodiment can be less likely to fall down.

Third Embodiment

The biometric information acquisition device 1 according to the first and second embodiments described above is described as an example in which the biometric information acquisition device 1 alone performs the processing of acquiring the finger image of the user and the biometric authentication processing based on the biometric information on the user. An example will be described in which a biometric authentication system 100 according to a third embodiment performs the processing of acquiring a finger image of a user by at least one biometric information acquisition device 1A, 3, and so on, and performs the biometric authentication processing based on the finger image of the user by an authentication device 2 connected to be capable of data communication via a network NW. Configurations similar to those of the biometric information acquisition device 1 according to the first and second embodiments are denoted by the same reference numerals, and a description thereof is omitted.

The biometric authentication system 100 according to the third embodiment includes at least one biometric information acquisition device 1A, 3, and so on, the authentication device 2, and the network NW.

Each of the biometric information acquisition devices 1A, 3, and so on performs encryption processing on the acquired finger image of the user, and transmits the encrypted image to the authentication device 2 connected to be capable of the data communication via the network NW. The authentication device 2 extracts the biometric information on the user from the finger image of the user transmitted from each of the biometric information acquisition devices 1A, 3, and so on. The authentication device 2 executes the user authentication based on the extracted biometric information on the user, and transmits an authentication result of the user authentication to each of the biometric information acquisition devices 1A, 3, and so on connected to be capable of the data communication via the network NW. Each of the biometric information acquisition devices 1A, 3, and so on outputs the authentication result transmitted from the authentication device 2 to the monitor MN.

That is, in the biometric authentication system 100 according to the third embodiment, steps St1 to St3 in the example of the operation procedure of the biometric information acquisition device 1 according to the first embodiment shown in FIG. 8 are executed by the biometric information acquisition devices 1A, 3, and so on, and the authentication device 2 executes the processing of steps St3 to St7.

The biometric information acquisition device 1A further includes a communication unit 20. The communication unit 20 is connected to a communication unit 30 in the authentication device 2 via the network NW to be capable of performing wireless or wired communication, and executes transmission and reception of data. Here, the wireless communication is, for example, communication via a wireless local area network (LAN) such as Wi-Fi (registered trademark). The communication unit 20 transmits the encrypted finger image of the user output from the processor 21 to the authentication device 2, and outputs the authentication result transmitted from the authentication device 2 to the processor 21.

One or more biometric information acquisition device 3 and so on are each connected to the authentication device 2 via the network NW to be capable of the data communication. The biometric information acquisition devices 3 and so on each acquire (capture an image of) a finger image including the biometric information on the user, perform the encryption processing on the acquired finger image, and transmit the encrypted finger image of the user to the authentication device 2. The biometric information acquisition devices 3 and so on each output, to a monitor (not shown), an authentication result generated by the authentication device 2 for the transmitted finger image. Since an internal configuration of each of the biometric information acquisition devices 3 and so on is the same as that of the biometric information acquisition device 1A, the description thereof is omitted.

Figure 10:
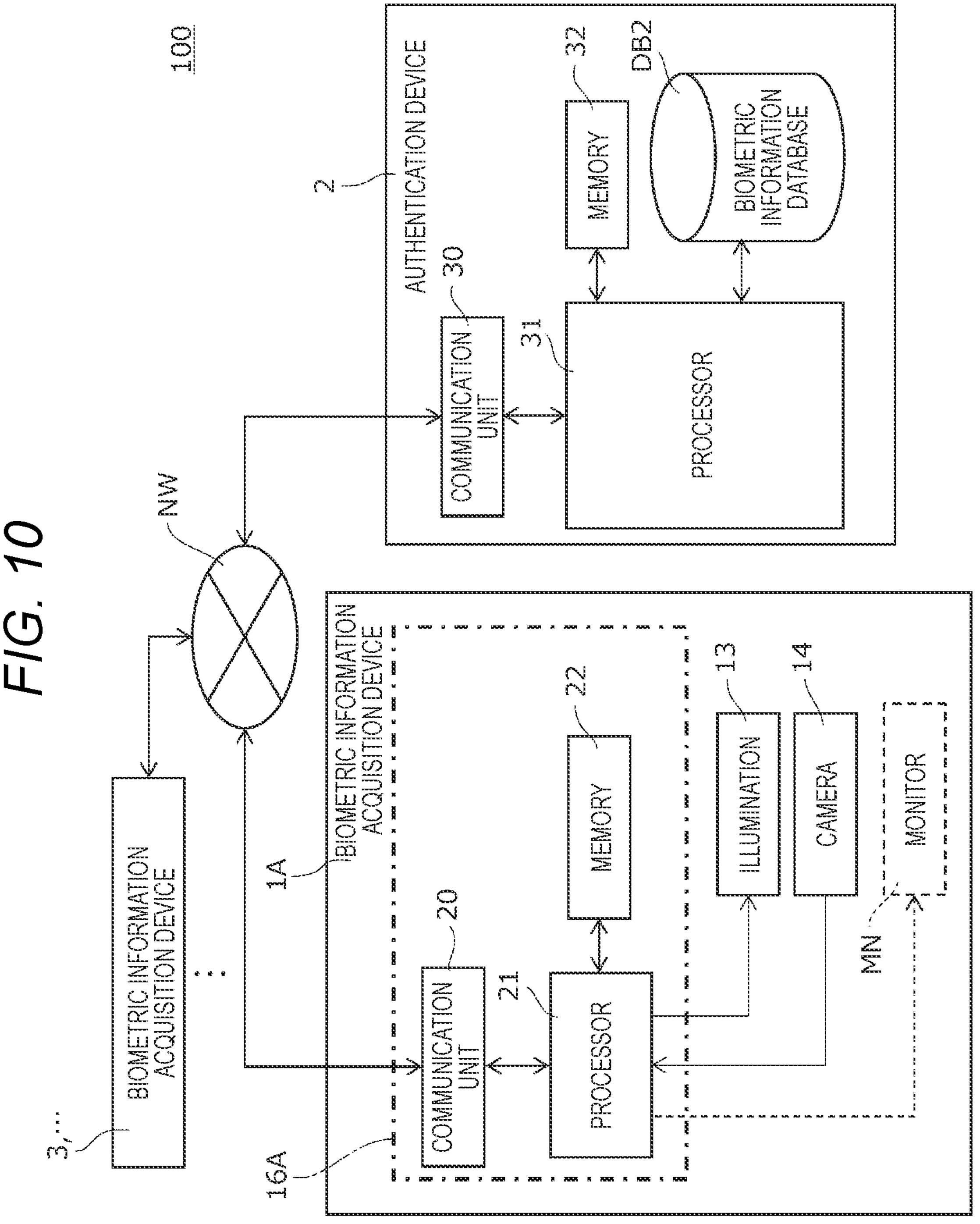
FIG. 10 is a diagram showing an example of an internal configuration of a biometric authentication system according to a third embodiment.
Figure 11:
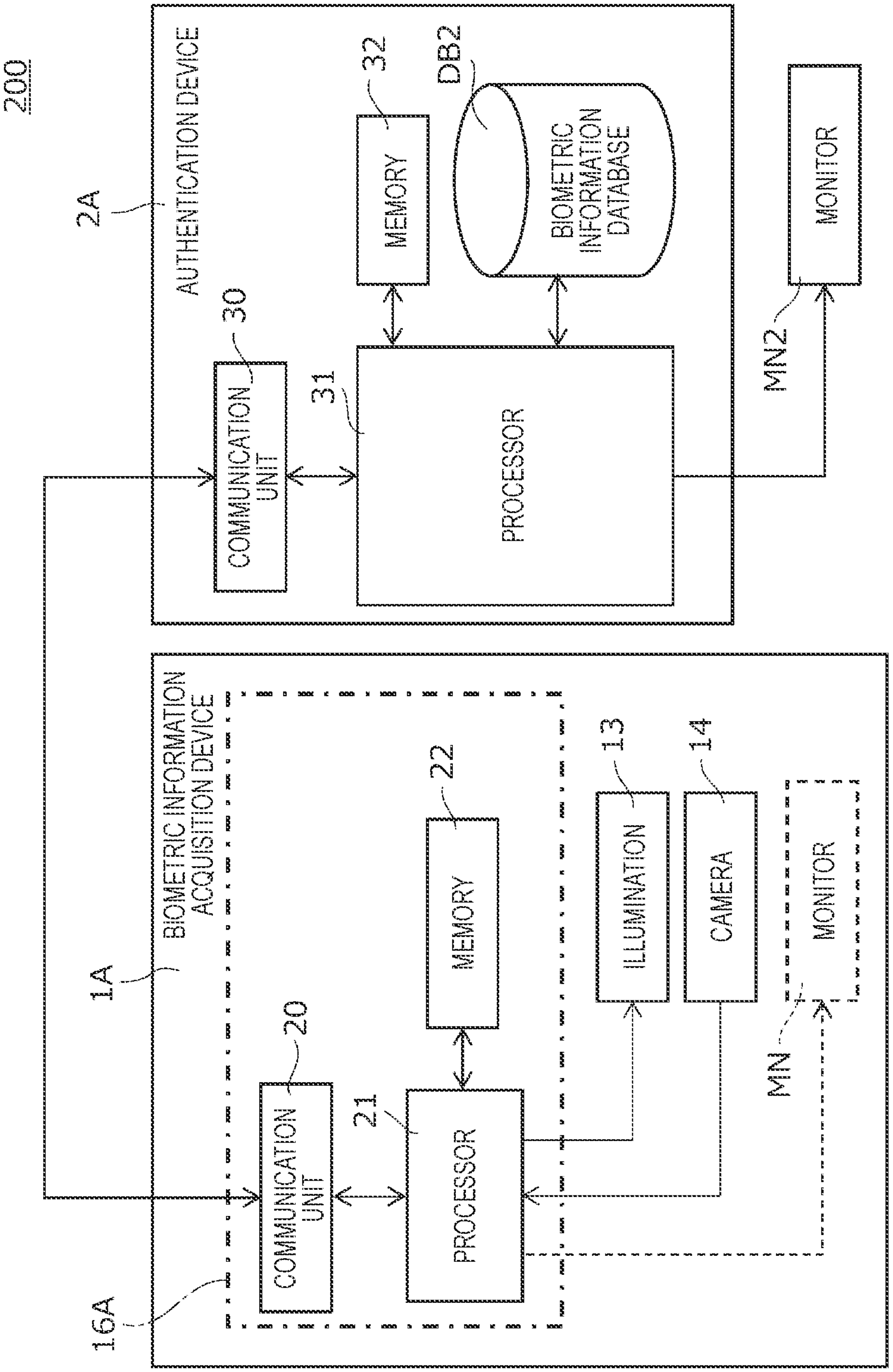
FIG. 11 is a diagram showing an example of an internal configuration of a biometric authentication system according to a fourth embodiment.

The authentication device 2 extracts the biometric information on the user by using the finger image of the user transmitted from each of the plurality of biometric information acquisition devices 1A, 3, and so on via the network NW. The authentication device 2 collates the extracted biometric information with the biometric information on a plurality of users registered in advance by an administrator or the like of the biometric authentication system 100 or the biometric information acquisition devices. The authentication device 2 determines whether the extracted biometric information matches any of the biometric information on the plurality of registered users, executes the user authentication processing, and transmits a determination result to each biometric information acquisition device. The authentication device 2 includes a communication unit 30, a processor 31, a memory 32, and a biometric information database DB2. Although an example in which the biometric information database DB2 shown in FIG. 10 is integrally formed with the authentication device 2 is illustrated as an example, the biometric information database DB2 is configured as an external storage device that is implemented separately from the authentication device 2 and is externally connected to be capable of the data communication.

The communication unit 30 is connected to the communication unit in each of the plurality of biometric information acquisition devices 1A, 3, and so on via the network NW to be capable of performing wireless or wired communication, and executes transmission and reception of data. The communication unit 30 outputs the finger image of the user transmitted from each biometric information acquisition device to the processor 31, and transmits the authentication result output from the processor 31 to each biometric information acquisition device. The authentication result transmitted to each biometric information acquisition device may be subjected to the encryption processing.

The processor 31 is formed using, for example, a CPU or an FPGA, and executes various kinds of processing and controls in cooperation with the memory 32. Specifically, the processor 31 executes a program by referring to a program and data held in the memory 32, thereby implementing functions related to the extraction processing of the biometric information and the user authentication processing.

The memory 32 includes, for example, a RAM as a work memory used when each processing of the processor 31 is executed, and a ROM that stores a program and data that define an operation of the processor 31. The RAM temporarily stores data or information generated or acquired by the processor 31. The program that defines the operation of the processor 31 is written into the ROM.

The biometric information database DB2 stores (registers), in association with the biometric information on each user, information (for example, a name, an identification number, and a face image) related to the plurality of users registered in advance by an administrator or the like of the biometric authentication system 100 or each of the biometric information acquisition devices.

The network NW connects each of the biometric information acquisition devices 1A, 3, and so on to the authentication device 2 to be capable of performing the wireless communication or the wired communication.

As described above, the biometric authentication system 100 according to the third embodiment can execute the user authentication processing based on the finger image acquired (imaged) by each of the plurality of biometric information acquisition devices 1A, 3, and so on by one authentication device 2. A time required for the user authentication processing executed by the authentication device 2 is much shorter compared to the time required for imaging of the finger image (that is, from when the user inserts the hand into the imaging space 18 until the finger image is imaged). Therefore, the biometric authentication system 100 can perform more user authentication in a shorter time by capturing images of the finger images of the users by the plurality of biometric information acquisition devices 1A, 3, and so on.

Fourth Embodiment

As described above, an example is described in which the biometric authentication system 100 according to the third embodiment performs the processing of acquiring the finger image of the user by at least one biometric information acquisition device 1A, 3, and so on, and performs the biometric authentication processing based on the finger image of the user by the authentication device 2 connected to be capable of the data communication via the network NW. An example will be described in which a biometric authentication system 200 according to a fourth embodiment performs processing of acquiring a finger image of a user by one biometric information acquisition device 1A and performs the biometric authentication processing based on the finger image of the user by an authentication device 2A connected to be capable of data communication. Configurations similar to those of the biometric information acquisition devices 1 and 1A and the authentication device 2 according to the first to third embodiments are denoted by the same reference numerals, and a description thereof is omitted.

The biometric authentication system 200 according to the fourth embodiment includes the biometric information acquisition device 1A and the authentication device 2A. The biometric information acquisition device 1A performs encryption processing on the acquired finger image of the user, and transmits the encrypted image to the authentication device 2A connected to be capable of the data communication. The encryption processing is not essential, and may be omitted. The authentication device 2A extracts the biometric information on the user from the finger image of the user transmitted from the biometric information acquisition device 1A. The authentication device 2A executes user authentication based on the extracted biometric information on the user, and outputs an authentication result of the user authentication to a monitor MN2.

That is, in the biometric authentication system 200 according to the fourth embodiment, steps St1 to St3 in the example of the operation procedure of the biometric information acquisition device 1 according to the first embodiment shown in FIG. 8 are executed by the biometric information acquisition device 1A, and the authentication device 2A executes the processing of steps St3 to St7.

The authentication device 2A according to the fourth embodiment displays the authentication result on the monitor MN2. The monitor MN2 is not an essential component and may be omitted. For example, when the monitor MN2 is omitted, the authentication device 2A may transmit the authentication result of the user authentication to the biometric information acquisition device 1A and output the authentication result using the monitor MN.

As described above, the biometric authentication system 200 according to the fourth embodiment does not need to transmit and receive, via the network NW, the finger image of the user and personal information on the user included in the authentication result, and therefore, leakage of the personal information on the user can be more accurately prevented.

As described above, the biometric information acquisition devices 1 and 1A according to the first to fourth embodiments include the camera 14 that captures an image of the hand H of the user inserted into the imaging space 18, the illumination 13 that illuminates the inside of the imaging space 18 from above, the housing 11 that accommodates the camera 14 and the illumination 13, and the first opening 12 formed by cutting out a part of the housing 11 and provided in a substantially rectangular shape in a front view to form the imaging space 18.

As described above, the biometric information acquisition devices 1 and 1A according to the first to fourth embodiments can prevent the illumination light of the illumination 13 from directly entering the eyes of the user by illuminating, by the illumination 13 from above, a part of the hand H or the finger of the user accommodated in the housing 11. In addition, since the illumination light of the illumination 13 does not directly enter the eyes of the user, the biometric information acquisition devices 1 and 1A can increase the light amount of the illumination 13. In addition, since an exposure time of the camera 14 can be set shorter by increasing the light amount of the illumination 13, the biometric information acquisition device 1 and 1A can capture an image of the finger image with reduced camera shake even in a state in which the hand of the user is not completely stationary. Therefore, since the biometric information acquisition devices 1 and 1A can capture an image of the finger image for the biometric authentication even when the hand H or a part of the finger of the user is imaged in a non-contact state, it is possible to improve authentication accuracy of the biometric authentication using the biometric information. Further, the biometric information acquisition devices 1 and 1A can capture an image of the finger image in which the camera shake is reduced, thereby preventing occurrence of re-imaging and shortening a time for the user to hold the hand H, thereby further improving usability.

As described above, the housing 11 in the biometric information acquisition devices 1 and 1A according to the first to fourth embodiments has the second opening 15 above the imaging space 18. The illumination 13 illuminates the inside of the imaging space 18 from above the second opening 15. Accordingly, the biometric information acquisition devices 1 and 1A according to the first to fourth embodiments can prevent the illumination light of the illumination 13 from directly entering the eyes of the user by illuminating, by the illumination 13 from above, a part of the hand H or the finger of the user accommodated in the housing 11.

As described above, the housing 11 of the biometric information acquisition devices 1 and 1A according to the first to fourth embodiments has the first opening 12 between a top surface of the housing 11 and a bottom surface of the housing 11. Accordingly, since the biometric information acquisition devices 1 and 1A according to the first to fourth embodiments can capture an image of the hand H of the user that is inserted into the imaging space 18 provided in the housing 11 and illuminated from above by the illumination 13, and since light from a light source installed around the biometric information acquisition devices 1 and 1A is less likely to be received, the finger image more suitable for the biometric authentication can be acquired.

As described above, the height H1 of the imaging space 18 of the biometric information acquisition devices 1 and 1A according to the first to fourth embodiments is equal to or less than the total height of the depth of field H2 of the camera 14 and the thickness H3 of the finger UH of the user. Accordingly, in the biometric information acquisition devices 1 and 1A according to the first to fourth embodiments, the hand H of the user inserted into the imaging space 18 is imaged within the depth of field H2 of the camera, and therefore, it is possible to efficiently acquire the finger image in which a part of the finger is in focus. Therefore, the biometric information acquisition devices 1 and 1A can further prevent the occurrence of re-imaging and shorten the time for the user to hold the hand H, thereby further improving usability.

As described above, the first openings 12A and 12B of the biometric information acquisition devices 1 and 1A according to the first to fourth embodiments are formed on the front surface side of the housing 11, and opening upper end portions of the first openings 12A and 12B in the front view (that is, a peripheral edge portion on the top surface side of opening peripheral edge portions of the first opening 12) are formed to be positioned on a top surface side of the housing 11 from a back surface to a front surface of the housing 11. Accordingly, in the biometric information acquisition devices 1 and 1A according to the first to fourth embodiments, the opening positions of the first openings 12A and 12B are higher on the front surface of the housing 11 into which the insertion of the hand H of the user is inserted (that is, the opening position is formed at a position having the highest position in the Z direction on the front surface). Therefore, the user can easily insert the hand H into the imaging space 18 from the front surface of the housing 11 through the first openings 12A and 12B.

As described above, the first opening 12A of the biometric information acquisition device 1 or 1A according to the first to fourth embodiments is formed on the front surface side of the housing 11, and the opening height H4 of the first opening 12A in a side view is formed such that the opening height increases from a back surface to a front surface of the housing 11. Accordingly, in the biometric information acquisition devices 1 and 1A according to the first to fourth embodiments, the opening height of the first opening 12A is the highest in the front surface of the housing 11 into which the insertion of the hand H of the user is inserted. Therefore, the user can easily insert the hand H into the imaging space 18 from the front surface of the housing 11 through the first opening 12A.

As described above, the second openings 15, 15A, and 15B of the biometric information acquisition devices 1 and 1A according to the first to fourth embodiments are smaller than an angle of view of the camera 14 (that is, the region RA1 shown in FIG. 6). Accordingly, the biometric information acquisition devices 1 and 1A according to the first to fourth embodiments can more efficiently acquire a finger image that does not include a region outside of the angle of view of the camera 14.

As described above, the second openings 15, 15A, and 15B of the biometric information acquisition devices 1 and 1A according to the first to fourth embodiments are smaller than an illumination range of the illumination 13 (that is, the region RA1 shown in FIG. 6). Accordingly, the biometric information acquisition devices 1 and 1A according to the first to fourth embodiments can more efficiently acquire a finger image obtained by capturing an image of the hand H or the finger UH of the user illuminated by the illumination 13.

As described above, the biometric information acquisition devices 1 and 1A according to the second to fourth embodiments further include the mirrors 19, 19A, and 19B that reflect the illumination light. The mirrors 19, 19A, and 19B reflect the light of the illumination 13 and illuminate the inside of the imaging space 18 from above. Accordingly, in the biometric information acquisition devices 1 and 1A according to the second to fourth embodiments, since a degree of freedom in arrangement of the illumination 13 can be secured, a height dimension of the housing 11 can be further reduced by the arrangement of the illumination 13, or a height of the center of gravity of the housing 11 can be lowered toward the bottom surface side (the −Z direction).

As described above, the biometric information acquisition devices 1 and 1A according to the second to fourth embodiments further include mirrors 19, 19A, and 19B that reflect the hand in the imaging space 18. The camera 14 captures an image of the hand H of the user reflected on the mirrors 19, 19A, and 19B. Accordingly, the biometric information acquisition devices 1 and 1A according to the second to fourth embodiments can secure a sufficient imaging distance (that is, the predetermined distance L) between the camera 14 and a part of the hand H or the finger of the user by capturing an image of the hand H or the finger UH of the user reflected on the mirror 19, and therefore, it is possible to reduce a size of the biometric information acquisition devices 1 and 1A while maintaining the height of the depth of field H2.

As described above, the biometric information acquisition devices 1 and 1A according to the first to fourth embodiments further include the monitor MN (an example of a display unit) that prompts a palm of the user to be inserted toward the top surface side of the housing 11. Accordingly, the biometric information acquisition devices 1 and 1A according to the first to fourth embodiments can present, to the user, an orientation of the palm at the time of insertion of the hand H.

As described above, the housing 11 of the biometric information acquisition device 1 or 1A according to the first to fourth embodiments further includes the control unit 16 or the power supply unit 17 (an example of a gravity center portion) on a bottom surface side than the imaging space 18. Accordingly, the biometric information acquisition devices 1 and 1A according to the first to fourth embodiments can adjust the height of the center of gravity of the housing 11 to a lower position (that is, the bottom surface side of the housing 11). Accordingly, even when an external force is applied to the side surface of the housing 11 (for example, when the hand H of the user comes into contact with or collides with the side surface of the housing 11), the biometric information acquisition devices 1 and 1A are less likely to fall down.

Although various embodiments have been described above with reference to the accompanying drawings, the present disclosure is not limited thereto. It is apparent to those skilled in the art that various modifications, corrections, substitutions, additions, deletions, and equivalents can be conceived within the scope described in the claims, and it is understood that such modifications, corrections, substitutions, additions, deletions, and equivalents also fall within the technical scope of the present disclosure. In addition, components in the various embodiments described above may be combined freely in a range without deviating from the spirit of the disclosure.

The present application is based on a Japanese patent application (Japanese Patent Application No. 2020-185816) filed on Nov. 6, 2020, and the contents thereof are incorporated herein by reference.

INDUSTRIAL APPLICABILITY

The present disclosure is useful as a presentation of a biometric information acquisition device capable of reducing dazzle due to illumination light at the time of capturing an image of a finger image used for biometric authentication and stably acquiring a finger image even in a non-contact manner.

REFERENCE SIGNS LIST

1, 1A: biometric information acquisition device
11: housing
12, 12A, 12B: first opening
13: illumination
14: camera
15, 15A, 15B: second opening
16: control unit
17: power supply unit
18: imaging space
19: mirror
21: processor
22: memory
H1: height
H2: depth of field
H3: thickness of finger
MN: monitor
H: hand
UH: finger

What is claimed is:

1. A biometric information acquisition device, comprising:
- a housing including a bottom surface side, a top surface side, a front surface side, a back surface side, and an opening in the front surface side between the bottom surface side and the top surface side, the opening defining an imaging space within the housing;
- a camera disposed in the housing, the camera being configured to capture an image of a palm of a hand of a user when inserted into the imaging space with the palm facing the top surface side;
- an illumination disposed in the housing between the top surface side and the opening, the illumination being configured to illuminate the imaging space from above; and
- a display configured to prompt the user to insert the palm into the imaging space with the palm facing the top surface side.

2. The biometric information acquisition device according to claim 1, wherein
the illumination has an annular shape.

3. The biometric information acquisition device according to claim 2, wherein
the camera is disposed within a periphery of the annular shape of the illumination, when viewed in an orthogonal direction from the top surface side.

4. The biometric information acquisition device according to claim 3, wherein
the camera is disposed in the housing between the illumination and the top surface side.

5. The biometric information acquisition device according to claim 4, wherein
the housing has a cylindrical shape.

6. The biometric information acquisition device according to claim 5, wherein
the opening includes a rectangular shape.

7. The biometric information acquisition device according to claim 6, wherein
edges of the rectangular shape are chamfered.

8. The biometric information acquisition device according to claim 1, wherein
the display is between the opening and the top surface side.

9. The biometric information acquisition device according to claim 8, wherein
the display and the opening are centered on the front surface side.

10. The biometric information acquisition device according to claim 1, wherein
the camera is disposed closer to the bottom surface side than the illumination.

11. The biometric information acquisition device according to claim 10, further comprising:

a mirror disposed in the housing, the mirror being configured to reflect light from the illumination toward the palm of the hand of the user when inserted into the imaging space with the palm facing the top surface side, wherein the mirror is disposed in the housing between the camera and the top surface side.

12. The biometric information acquisition device according to claim 10, wherein the camera and the mirror overlap, when viewed in an orthogonal direction from the front surface side.

13. The biometric information acquisition device according to claim 10, wherein each of the camera and the illumination overlap with the mirror, when viewed in an orthogonal direction from the front surface side.

14. The biometric information acquisition device according to claim 1, wherein the housing includes a second opening above the imaging space, the camera being between the second opening and the top surface side, and the illumination illuminates the inside of the imaging space from above the second opening.

15. The biometric information acquisition device according to claim 14, wherein the second opening is smaller than an angle of view of the camera.

16. The biometric information acquisition device according to claim 14, wherein the second opening is smaller than an illumination range of the illumination.

17. The biometric information acquisition device according to claim 1, wherein a height of the opening increases from the back surface side of the housing to the front surface side of the housing.

18. The biometric information acquisition device according to claim 1, wherein the opening includes an elliptical shape.

19. The biometric information acquisition device according to claim 1, further comprising:

a mirror disposed in the housing, the mirror being configured to reflect light from the illumination toward the palm of the hand of the user when inserted into the imaging space with the palm facing the top surface side, wherein the mirror is further configured to reflect the palm of the hand in the imaging space, and the camera is configured to capture the image of the palm of the hand reflected by the mirror.

20. The biometric information acquisition device according to claim 1, further comprising:

a controller disposed in the housing between the opening and the bottom surface side; and a power supply disposed in the housing between the opening and the bottom surface side.

* * * * *